(12) United States Patent
Kempe

(10) Patent No.: US 6,834,536 B2
(45) Date of Patent: Dec. 28, 2004

(54) PROBE FOR MEASURING ALCOHOL IN LIQUIDS

(75) Inventor: Eberhard Kempe, Berlin (DE)

(73) Assignee: Biotechnologie Kempe GmbH, Berlin (DE)

( * ) Notice: Subject to any disclaimer, the term of this patent is extended or adjusted under 35 U.S.C. 154(b) by 0 days.

(21) Appl. No.: 10/410,806

(22) Filed: Apr. 10, 2003

(65) Prior Publication Data

US 2003/0192368 A1 Oct. 16, 2003

(30) Foreign Application Priority Data

Apr. 15, 2002 (DE) .......................................... 102 16 653

(51) Int. Cl.[7] .............................................. G01N 33/00
(52) U.S. Cl. ..................... 73/61.41; 73/19.01; 73/19.1; 73/19.12; 73/61.76; 250/339.06; 250/339.12
(58) Field of Search .............................. 73/19.01, 19.1, 73/19.12, 61.41, 61.76; 250/339.06, 339.12, 339.13

(56) References Cited

U.S. PATENT DOCUMENTS

| | | | | |
|---|---|---|---|---|
| 4,468,948 A | * | 9/1984 | Nakayama | .................. 73/19.1 |
| 4,517,135 A | * | 5/1985 | Szerenyi et al. | ............ 261/104 |
| 5,331,845 A | * | 7/1994 | Bals et al. | .................. 73/61.43 |
| 6,003,362 A | * | 12/1999 | Dieckmann et al. | ........ 73/19.12 |
| 6,138,497 A | * | 10/2000 | Nix et al. | ................... 73/19.06 |
| 6,526,805 B1 | * | 3/2003 | Babes-Dornea et al. | ... 73/19.12 |

FOREIGN PATENT DOCUMENTS

| | | |
|---|---|---|
| DE | 199 59 271 A1 | 6/2001 |
| DE | 100 25 686 A1 | 11/2001 |
| EP | 0 174 417 B1 | 3/1986 |

* cited by examiner

Primary Examiner—Daniel S. Larkin
(74) Attorney, Agent, or Firm—McGlew and Tuttle, P.C.

(57) ABSTRACT

A probe (1) for quantitatively measuring volatile components of a liquid (2) includes a measurement gas space (3) separated from the liquid (4) by a permeation membrane (5). The membrane (5) is permeable for the volatile component, however nonpermeable for liquid. A selective gas detection system is arranged in the measurement gas space (3) for a defined volatile component. The gas detection system has an IR light source (6), an IR filter (7), (7') and an IR-sensitive light sensor (8), (8'). Light falls through the IR filter on the light sensor (8), (8'). The IR filter (7), (7') comprises a transmission window in the range of an alcohol-specific absorption band.

25 Claims, 1 Drawing Sheet

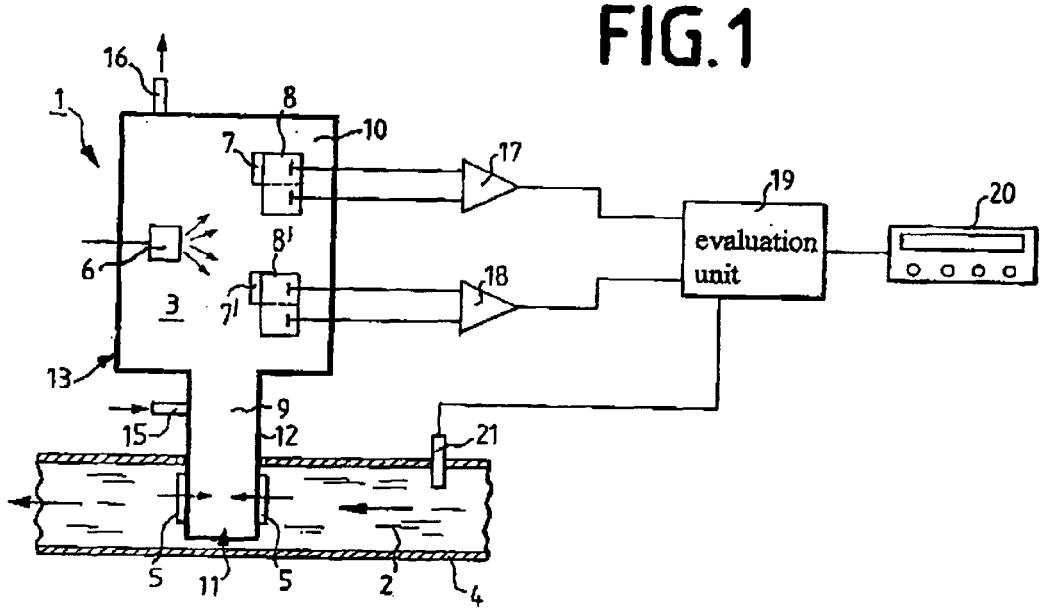
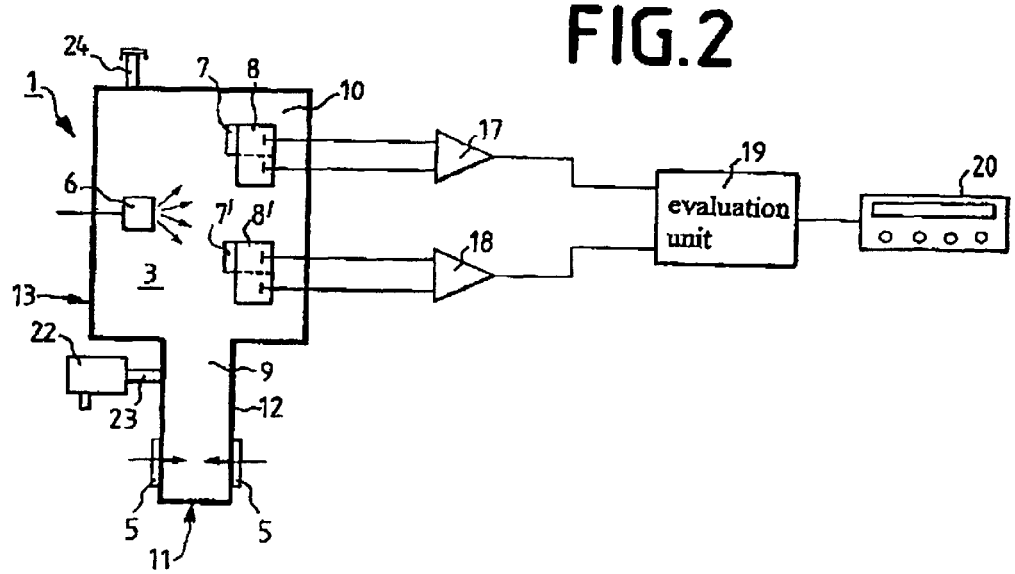

PROBE FOR MEASURING ALCOHOL IN LIQUIDS

FIELD OF THE INVENTION

The invention relates to a probe for quantitatively measuring volatile components of a liquid comprising a measurement gas space, said measurement gas space being separated from the liquid by a permeation membrane being permeable for the volatile component, however non-permeable for liquid, and comprising a selective gas detection system arranged in the measurement gas space for a defined volatile component.

BACKGROUND AND PRIOR ART

For monitoring, controlling and/or regulating certain chemical, biotechnological, food-processing, or pharmaceutical processes, it is necessary to determine and monitor on-line, in-line or off-line the alcohol content of a solution or suspension. Further, it is regularly desirable to simultaneously detect and monitor other volatile components of the solution or suspension, such as $CO_2$. An example of an economically important process is beer brewing.

Volatile components of a liquid may be, in addition to C1 to C6 alkyl monoalcohols, C1 to C8 hydrocarbons, C1 to C6 alkyl aldehydes, C1 to C6 alkyl ketones, C1 to C6 alkyl carboxylic acids, $CO_2$ and $O_2$. In the beer brewing technology, in particular C1 to C3 alkyl monoalcohols, in particular ethanol, $CO_2$, and/or $O_2$ have to be determined and monitored.

For instance from the documents EP 0 174 417 E1 and DE-199 59 271 A1 there are known in the art probes by means of which the alcohol content of a liquid-can be determined on-line or in-line. In the in so far known measures, alcohol determination is made by means of a solid state detector. A solid state detector typically comprises a semiconductor element, for instance on the basis tin oxide, at the surface of which alcohol is reacted, thus an electrical signal being generated that is fed to an evaluation circuitry. The in so far known technology is well proven. There is however a requirement for the determination of high alcohol contents, i.e. in the range from 2% v/v (referred to the liquid) to 20% v/v. With such high alcohol concentrations, measurements with solid-state detectors are however inaccurate or even impossible.

From the document DE 100 25 686 A1 it is known in the art of the beer brewing technology to simultaneously determine the alcohol content and the index of refraction of a liquid. In this approach, again a tin oxide sensor is used, with the above drawback. Further, this prior art sensor operates without a carrier gas with the consequence of a very high time constant.

TECHNICAL OBJECT OF THE INVENTION

The invention is based on the technical object to specify a probe, by means of which high alcohol concentrations can reliably be determined

BASIC PRINCIPLES OF THE INVENTION AND PREFERRED EMBODIMENTS

For achieving the above technical object, the invention teaches that the gas detection system comprises an IR light source, an IR filter, and an IR-sensitive light sensor, light falling exclusively through the IR filter on the light sensor, and that the IR filter comprises a transmission window in the range of an alcohol-specific absorption band.

The term of the IR-sensitive light sensor comprises, in addition to photosensors, also thermal sensors, for instance pyroelectric sensors. An IR light source transmits IR light in the range of the transmission window. A transmission window is the property of a component to only let pass a wavelength range definable by the width at half-maximum (referred to maximum transmission) about a defined center wavelength. The term wavelength will in the following always refer to the center wavelength. Transmission windows will not overlap, if the widths at half-maximum do not overlap.

The invention is first of all based on the finding that high alcohol contents can also be measured with the usual permeation membranes. Subsequently thereto, it was found that by means of an IR absorption measurement a linear or easily linearizable (for instance by calibration with a transfer function obtained by measurement of a reference solution or of several reference solutions) signal is obtained, at concentrations of up to 20% v/v and higher in the liquid. Of particular importance is here that not only an increase of a carrier gas flow through the measurement gas space is not necessary anymore (with this measure, semiconductor detectors can also be used for higher alcohol contents), rather a carrier gas flow may completely be left out. This permits the use of mobile portable probes, since a carrier gas source needs not be taken along. Prior to such a measurement or between two measurements, a rinsing only of the measurement gas space needs be performed, for instance by ambient air.

The transmission window suitably is provided at a wavelength of 1.0 to 3.0 $\mu$m, preferably 1.5 to 2.5 $\mu$m, in particular 2.0 to 2.2 $\mu$m.

The IR filter can in principle be located at different places. If the filter is arranged immediately at the IR light source, then only light having the wavelengths of the transmission window will pass the measurement gas space or parts thereof. Then the light sensor needs not be wavelength-selective. It is however preferred that the IR filter is arranged immediately in front of the light sensor. Then, light having wavelengths of the complete IR range will pass the measurement gas space or parts thereof, whereas the combination of light sensor and IR filter forms a wavelength-sensitive light sensor. In any case it is recommended that the light sensor is protected or shielded from foreign light.

For stationary applications, for instance the on-line or in-line measurement in a flowing liquid, with the permeation membrane being immersed in the liquid, it is preferred that the measurement gas space is passed by a preferably continuous carrier gas flow, i.e. the alcohol molecules being convectively transported through the measurement gas space. Carrier gases may be air, nitrogen, etc. By adjusting a defined carrier gas flow, a very high accuracy is achieved. The liquid may pass by the permeation membrane (in-line measurements) or rest (laboratory measurement of a sample).

For mobile or portable embodiments of the invention it is however preferred that no carrier gas is used. The only measure taken is that prior to a measurement the measurement gas space is rinsed with for instance air. A small pump may be provided therefor, said pump being connected to a rinse gas inlet. Suitably a rinse gas outlet is also provided. After rinsing, the rinse gas inlet and the rinse gas outlet are closed. The permeation membrane is then immersed into a taken liquid sample, and that so long until a constant measurement value is achieved, i.e. a balance between the alcohol content of the sample and the alcohol content of the measurement gas space exists. The transportation of the alcohol molecules in the gas phase thus takes place in a purely diffusive manner.

In an embodiment of the invention having an independent importance, a second light sensor and a second IR filter, preferably immediately in front of the second light sensor, are provided in the measurement gas space, the second IR filter having a transmission window in the range of a $CO_2$-specific absorption band, and the transmission windows of the first IR filter and of the second IR filter do not overlap. In this embodiment, $CO_2$ and alcohol can be measured with a single probe. In the case of the carrier gas-free operation and rinsing with air, there takes place of course a zero measurement of $CO_2$, the value of which is subtracted from the measured value for the determination of the $CO_2$ content of the liquid. Instead of $CO_2$ or in addition thereto, the probe can be configured for the simultaneous measurement of further volatile components by addition of light sensors and filters with corresponding transmission windows.

In the case of the $CO_2$ measurement it is preferred that the transmission window of the second IR filter is provided at a wavelength from 3.0 to 5.0 µm, preferably from 4.0 to 5.0 µm, in particular from 4.1 to 4.5 µm.

The measurement of further components, in particular $CO_2$ in addition to alcohol, may be provided in different ways. The measurement gas space may comprise: i) a permeation gas space, ii) a first IR measurement cuvette with a first IR light source, a first IR filter, and a first light sensor, and iii) a second IR measurement cuvette with a second IR light source, a second IR filter, and a second light sensor, wherein the permeation gas space, the first IR measurement cuvette, and the second IR measurement cuvette are connected to one another in a gas diffusive or convective manner, and wherein the transmission windows of the first IR filter and the second IR filter do not overlap one another and are provided in a range of an alcohol-specific and a $CO_2$-specific absorption band. Alternatively, the measurement gas space may comprise: i) a permeation gas space, and ii) a single IR measurement cuvette with an IR light source, a first IR filter, a second IR filter, and at least one light sensor, wherein the permeation gas space and the IR measurement cuvette are connected to one another in a gas-diffusive or convective manner, and wherein the transmission windows of the first IR filter and the second IR filter do not overlap one another and are provided in a range of an alcohol-specific and a $CO_2$-specific absorption band. In the latter case, a particularly simple design is achieved.

A further simplification of the design and reduction of the dimensions and weight is obtained, if the probe comprises a probe finger with a probe finger space separated by the permeation membrane from the liquid and a probe body carrying the probe finger, the at least one IR measurement cuvette being arranged in the probe body and being connected with the probe finger space in a diffusive or convective manner. Alternatively, the probe may comprise a probe finger with a probe finger space separated by the permeation membrane from the liquid and a probe body carrying the probe finger with a probe body gas space, and at least one IR measurement cuvette carried by the probe body, the probe finger space, the probe body space, and the IR cuvette being connected to one another in a diffusive or convective manner.

In the measurement gas space further detectors for the most various volatile components may be provided. Thus, it is also possible to provide an alcohol-specific solid-state gas sensor in the measurement gas space, in particular in the probe body space, for the measurement of low alcohol concentrations (up to 2% v/v).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 1 is a schematic view and diagram of a probe according to the invention for the combined measurement of alcohol and $CO_2$, and FIG. 2 is a schematic view and diagram of a probe according to the invention in a portable version.

DESCRIPTION OF THE INVENTION

Referring to the drawings in particular, a probe 1 is shown for quantitatively measuring volatile components of a liquid 2 flowing through a tube 4, and having a measurement gas space 3. The measurement gas space 3 is separated from the liquid 2 by a permeation membrane 5 being permeable for the volatile component, not however for the liquid. A gas detection system is provided comprising an IR light source 6, two IR filters 7, 7', and two IR-sensitive light sensors 8, 8', the light falling through the IR filters 7, 7' on the light sensors 8, 8'. The IR filter 7 has a transmission window in the range of an alcohol-specific absorption band, namely at 2.09 µm. The IR filter 7' has a transmission window in the range of a $CO_2$-specific absorption band, namely at 4.3 µm. The light sensors 8, 8' are pyroelectric detectors and for instance obtainable from the company Laser Components GmbH, Germany (for instance from the LIE series). The IR filters 7, 7' are integrated or arranged immediately in front of the light sensors 8, 8'. The detectors are double detectors, i.e. comprise two sensors each, one of them being shaded off by an IR filter 7, 7'.

In the embodiment, a device for in-line measuring, the measurement gas space 3 is passed by a continuous carrier gas flow, for this purpose a carrier gas inlet 15 and a carrier gas outlet 16 being provided.

In detail, the measurement gas space 3 comprises: i) a permeation gas space 9, ii) a single IR measurement cuvette 10 with an IR light source 6, a first IR filter 7, a second IR filter 7' and at least two light sensors 8, 8', the permeation gas space 9, and the IR measurement cuvette 10 being connected to one another by means of the carrier gas flow in a convective manner. A probe finger 11 immersing in the liquid 2 is provided, with a probe finger space 12 separated by the permeation membrane 5 from the liquid 2 and a probe body 13 carrying the probe finger 11, the IR measurement curette 10 being arranged in the probe body 13.

Further, amplifiers 17, 18 connected to the light sensors 8, 8' are provided, the output signal of said amplifiers being fed to an evaluation unit 19. In the evaluation unit 19, the signals are transformed under consideration of stored calibration curves into concentrations, referred to the concentrations in the liquid, and are displayed in a display and operating unit 20. To the evaluation unit 19 is further connected a temperature sensor 21, the measured liquid temperature value of which is taken into account when calculating the concentration.

In FIG. 2 is shown a portable variant of a probe 1 according to the invention. The essential elements correspond to those of FIG. 1, and reference is made thereto in this respect. As a difference, there is however no carrier gas inlet 15 and no carrier gas outlet 16. Rather, a rinse air pump 22 is provided, the pressure side of which is connected by a rinse air inlet 23 with the measurement gas space 3. The suction side is connected to ambient air. Further, a rinse air outlet 24 is provided, which can be closed. Rinse air inlet 23 and rinse air outlet 24 may be identical in design with the carrier gas inlet 15 and the carrier gas outlet 16, so that the probe 1 can be operated in both variants, in-line or in laboratory operation, or mobile.

While specific embodiments of the invention have been shown and described in detail to illustrate the application of the principles of the invention, it will be understood that the invention may be embodied otherwise without departing from such principles.

What is claimed is:

1. A probe for quantitatively measuring volatile components of a liquid, the probe comprising:
    a permeation membrane permeable for the volatile component, however, non-permeable for liquid;
    a measurement gas space separated from the liquid by the permeation membrane;
    a selective gas detection system arranged in the measurement gas space for a defined volatile component, the gas detection system comprising an IR light source, an IR filter, and an IR-sensitive light sensor with light falling through the IR filter on the light sensor, the IR filter comprising a transmission window in the range of an alcohol-specific absorption band; and
    a probe finger with a probe finger space separated by the permeation membrane from the liquid and a probe body carrying the probe finger, wherein at least one IR measurement cuvette is arranged in the probe body and connected with the probe finger space in a diffusive or convective manner.

2. A probe according to claim 1, wherein the transmission window is provided at a wavelength of 1.0 to 3.0 $\mu$m.

3. A probe according to claim 1, wherein the transmission window is provided at a wavelength of 1.5 to 2.5 $\mu$m.

4. A probe according to claim 1, wherein the transmission window is provided at a wavelength of 2.0 to 2.2 $\mu$m.

5. A probe according to claim 1, wherein the IR filter is arranged immediately in front of the light sensor.

6. A probe according to claim 1, wherein the measurement gas space is passed by a continuous carrier gas flow.

7. A probe according to claim 1, wherein a second light sensor and a second IR filter immediately in front of the second light sensor, are provided in the measurement gas space, the second IR filter having a transmission window in the range of a $CO_2$-specific absorption band, and wherein the transmission windows of the first IR filter and of the second IR filter do not overlap.

8. A probe according to claim 7, wherein the transmission window of the second IR filter is provided at a wavelength from 3.0 to 5.0 $\mu$m.

9. A probe according to claim 7, wherein the transmission window of the second IR filter is provided at a wavelength from 4.0 to 5.0 $\mu$m.

10. A probe according to claim 7, wherein the transmission window of the second IR filter is provided at a wavelength from 4.1 to 4.5 $\mu$m.

11. A probe according to claim 1, wherein the measurement gas space comprises: i) a permeation gas space, ii) a single IR measurement cuvette with the IR light source, the IR filter, a second IR filter, the light sensor, and a second light sensor, wherein the permeation gas space and the IR measurement cuvette are connected to one another in a gas-diffusive or convective manner, and wherein the transmission windows of the IR filter and the second IR filter do not overlap one another and are provided in a range of an alcohol-specific and a $CO_2$-specific absorption band.

12. A probe according to claim 1, wherein the measurement gas space, in particular in a probe body space, an alcohol-specific solid-state gas sensor is provided.

13. A probe for quantitatively measuring volatile components of a liquid, the probe comprising:
    a permeation membrane permeable for the volatile component, however, non-permeable for liquid;
    a measurement gas space separated from the liquid by the permeation membrane;
    a selective gas detection system arranged in the measurement gas space for a defined volatile component, the gas detection system comprising an IR light source, an IR filter, and an IR-sensitive light sensor with light falling through the IR filter on the light sensor, the IR filter comprising a transmission window in the range of an alcohol-specific absorption band; and
    a probe finger with a probe finger space separated by the permeation membrane from the liquid, and a probe body carrying the probe finger with a probe body gas space and at least one IR measurement cuvette being carried by the probe body, the probe finger space, the probe body space and the at least one IR cuvette being connected to one another in a diffusive or convective manner.

14. A probe according to claim 13, wherein the transmission window is provided at a wavelength of 1.0 to 3.0 $\mu$m.

15. A probe according to claim 13, wherein the transmission window is provided at a wavelength of 1.5 to 2.5 $\mu$m.

16. A probe according to claim 13, wherein the transmission window is provided at a wavelength of 2.0 to 2.2 $\mu$m.

17. A probe according to claim 13, wherein the IR filter is arranged immediately in front of the light sensor.

18. A probe according to claim 13, wherein the measurement gas space is passed by a continuous carrier gas flow.

19. A probe according to claim 13, wherein a second light sensor and a second IR filter immediately in front of the second light sensor, are provided in the measurement gas space, the second IR filter having a transmission window in the range of a $CO_2$-specific absorption band, and wherein the transmission windows of the first IR filter and of the second IR filter do not overlap.

20. A probe according to claim 19, wherein the transmission window of the second IR filter is provided at a wavelength from 3.0 to 5.0 $\mu$m.

21. A probe according to claim 19, wherein the transmission window of the second IR filter is provided at a wavelength from 4.0 to 5.0 $\mu$m.

22. A probe according to claim 19, wherein the transmission window of the second IR filter is provided at a wavelength from 4.1 to 4.5 $\mu$m.

23. A probe according to claim 13, wherein the measurement gas space comprises: i) a permeation gas space, ii) a single IR measurement cuvette with the IR light source, the IR filter, a second IR filter, the light sensor, and a second light sensor, wherein the permeation gas space and the IR measurement cuvette are connected to one another in a gas-diffusive or convective manner, and wherein the transmission windows of the IR filter and the second IR filter do not overlap one another and are provided in a range of an alcohol-specific and a $CO_2$-specific absorption band.

24. A probe according to claim 13, wherein the measurement gas space, in particular in a probe body space, an alcohol-specific solid-state gas sensor is provided.

25. A probe for quantitatively measuring volatile components of a liquid, the probe comprising:

a permeation membrane permeable for the volatile component, however, non-permeable to the liquid;

a measurement gas space separated from the liquid by the permeation membrane;

a selective gas detection system arranged in the measurement gas space for a volatile component, the gas detection system comprising an IR light source, an IR filter and an IR-sensitive light sensor with light passing through the IR filter onto the light sensor, the IR filter having a transmission window in the range of an alcohol-specific absorption band;

a probe finger with a probe finger space separated by the permeation membrane from the liquid and a probe body carrying the probe finger, an IR measurement cuvette being arranged in the probe body and being connected with the probe finger space in a diffusive or convective manner.

* * * * *